(12) United States Patent
Van Dun et al.

(10) Patent No.: US 9,518,256 B2
(45) Date of Patent: *Dec. 13, 2016

(54) TOMATO WITH IMPROVED SHELF-LIFE

(75) Inventors: Cornelis Maria Petrus Van Dun, Roosendaal (NL); Pieter Martijn Eggink, Oostvoorne (NL); Dörthe Bettina Dräger, Den Hoorn (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 484 days.

This patent is subject to a terminal disclaimer.

(21) Appl. No.: 13/407,034

(22) Filed: Feb. 28, 2012

(65) Prior Publication Data

US 2012/0216308 A1    Aug. 23, 2012

Related U.S. Application Data

(63) Continuation-in-part of application No. PCT/EP2010/063253, filed on Sep. 9, 2010.

(30) Foreign Application Priority Data

Sep. 9, 2009 (EP) ..................................... 09169860

(51) Int. Cl.
   *C12N 15/01*  (2006.01)
   *C12N 5/04*   (2006.01)
   *A01H 5/08*   (2006.01)

(52) U.S. Cl.
   CPC ................. *C12N 15/01* (2013.01); *C12N 5/04* (2013.01); *A01H 5/08* (2013.01)

(58) Field of Classification Search
   USPC ..................................................... 800/317.4
   See application file for complete search history.

(56) References Cited

U.S. PATENT DOCUMENTS

| | | | |
|---|---|---|---|
| 4,843,186 | A | 6/1989 | Nahum |
| 6,429,299 | B1 | 8/2002 | Bowler et al. |
| 2012/0216308 | A1 | 8/2012 | Van Dun et al. |
| 2013/0291137 | A1* | 10/2013 | Van Dun et al. ............. 800/260 |

FOREIGN PATENT DOCUMENTS

WO   WO 2005/048692   6/2005

OTHER PUBLICATIONS

Peralta et al. Nomenclature for wild and cultivated tomatoes. TGC Report. 2006. 56: 6-12.*
Beckles. Factors affecting the postharvest soluble solids and sugar content of tomato (*Solanum lycopersicum* L.) fruit. Postharvest Biology and Technology. 2012. 63: 129-140.*
Giovannoni. Fruit ripening mutants yield insights into ripening control. Current Opinion in Plant Biology. 2007. 10: 283-289.*
Mutschler. PI 508291. Solanum lycopersicum—Oscar Pearson Hard Fruit. Germplasm Resources Information Network. 1987. pp. 1-2.*
Lambeth. PI 559913. Solanum lycopersicum—P3229. Germplasm Resources Information Network. 1991. pp. 1.*
Mustilli et al. Phenotype of the tomato high pigment-2 mutant is caused by a mutation in the tomato homolog of DEETIOLATED1. The Plant Cell. 1999. 11: 145-157.*
GenBank Accession No. AJ224356.1. Solanum lycopersicon tDET1 gene. Published Nov. 14, 2006. pp. 1-4.*
Wann. Physical characteristics of mature green and ripe tomato fruit of normal and firm genotypes. Journal of American Society of Horticulture Science. 1996. 121(3): 380-383.*
A. Barone, et al., High-Throughput Genomics Enhances Tomato Breeding Efficiency, Current Genomics (2009) vol. 10, p. 1-9.
Naveen Garg, et al., Genetics of Yield, Quality and Shelf Life Characteristics in Tomato Under Normal and Late Planting Conditions, Euphytica (2008) vol. 159, p. 275-288.
A.R. Schuelter, et al., Inheritance and Genetic Linkage Analysis of a Firm-Ripening Tomato Mutant, Plant Breeding (2002) vol. 121, p. 338-342.
Anna Seroczynska, et al., Genetic Analysis of Selected Tomato (*Lycopersicon esculentum* Mill.) Traits in Crosses Between Cultivated Lines and the Nor Mutant, J. Appl. Genetics (1998) vol. 39, No. 3, p. 259-273.
Andrew J. Thompson, et al., Molecular and Genetic Characterization of a Novel Pleiotropic Tomato-Ripening Mutant, Plant Physiology (1999) vol. 120, p. 383-389.
Levin, et al. "The tomato dark green mutation is a novel allele of the tomato homolog of the DEETIOLATED1 gene" Theor Appl Genet 106:454-460, 2003.
Soressi. "New spontaneous or chemically-induced fruit-ripening tomato mutants" Report of the Tomato Genetics Cooperative, 25:1-2, 1975.

* cited by examiner

*Primary Examiner* — Anne Kubelik
*Assistant Examiner* — Ashley K Buran
(74) *Attorney, Agent, or Firm* — Vedder Price P.C.; Thomas J. Kowalski; Deborah L. Lu

(57) ABSTRACT

The invention relates to a tomato plant the fruits of which have an improved shelf-life as compared to the fruits of a wild type tomato plant, obtainable by introgressing the increased shelf life trait from the mutant LePQ58 (deposit accession number NCIMB 41531) into a tomato plant with a normal shelf-life. The increased shelf-life may comprise a fruit that shows normal ripening having a fruit firmness at red ripe harvest that is increased by at least 31%, preferably by at least 42%, more preferably by at least 52%, even more preferably by at least 60%, most preferably by at least 70% as compared to a fruit having similar genetic background that lacks the trait of the invention.

7 Claims, 5 Drawing Sheets

TOMATO WITH IMPROVED SHELF-LIFE

RELATED APPLICATIONS AND INCORPORATION BY REFERENCE

This application is a continuation-in-part application of international patent application Serial No. PCT/EP2010/063253 filed 9 Sep. 2010, which published as PCT Publication No. WO 2011/042279 on 14 Apr. 2011, which claims benefit of European patent application Serial No. 09169860.5 filed 9 Sep. 2009.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to a tomato plant, the fruits of which have an improved shelf-life as compared to existing tomato fruits. The invention further relates to the progeny of such plants and to propagation material for obtaining such plants with an improved shelf-life. The invention also relates to germplasm that comprises the genomic information leading to the improved shelf-life trait of the invention and to the use of this germplasm.

BACKGROUND OF THE INVENTION

Commercial production of tomato aims for productivity combined with quality. Quality can be defined in different terms like flavour, taste, texture, mouth feel, appearance, shape, colour, soluble solids, nutritional compounds, disease resistance and shelf-life. During the ripening of fruits these quality traits can develop in various ways depending on the variety in combination with the growing conditions and postharvest treatments. Therefore, the end product, i.e. the fruit that is consumed, often is a compromise between all these traits.

Optimising fruit developmental traits contributes to the profitability of the commercial grower. Plant breeding has traditionally provided the growers with varieties bred for high productivity. Such varieties have been selected to enable the grower to maximise fruit biomass production under specific environmental conditions.

However, recently the fresh market of tomato has changed in the sense that in addition to the traditional varieties, products with improved quality traits like flavour, taste and texture are demanded. This has led to a revision of the breeding targets towards increased quality traits which are preferably combined with high productivity.

A key trait in this respect is shelf-life. Varieties of which harvested fruits can be stored for a longer period of time without losing texture and firmness can be harvested at a later developmental stage. This has the enormous advantage that quality traits can develop during the growth of the crop. In addition, fruits which can ripen without losing texture and firmness can be of interest for the fresh-cut market.

The combined value of the expressed quality traits can differ substantially between commercial varieties. A major obstacle in the improvement of the overall quality of harvested tomato fruits is caused by the fact that the development of quality traits like flavour, colour and taste is often incongruous with the desire to harvest fruits with a long shelf-life. A long shelf-life is required in order to avoid too much bruising during harvest and storage. As fruit ripening in terms of colouration and softening continues postharvest, a solution to this problem is often found by harvesting the tomato fruits at the mature green or breaker stage after which they will turn red during storage. The big advantage of such practice is that the fruits are still very firm at harvest and therefore have a high resistance against bruising. The fruits will reach the consumer red-coloured and undamaged. Although this is a practical solution to the shelf-life limitation, in cases where the products need to be stored for prolonged periods of time e.g. when long transportation distances are involved this approach is still inadequate.

A further and very important problem is that although colouration and softening develop postharvest, flavour and taste do not. Therefore the quality trait shelf-life seems to be in conflict with the quality traits flavour and taste. It is therefore desirable to improve tomatoes in such a way that quality traits like flavour and taste can develop preharvest in combination with a long shelf-life.

A further advantage of long shelf-life in tomato is related to the labour input required to harvest the fruits. Fruits with a normal shelf-life need to be picked as much as possible at the same developmental stage in order to prevent too much variation with respect to the post-harvest quality of the fruit due to variation in maturity. This can sometimes even be twice a day. In case long shelf-life tomatoes are available there is no need for such labour intensive harvesting, as irrespective of the developmental stage at harvest fruits will ripen and remain firm. In addition to the reduced labour input, flexibility in harvesting time allows to tailor the delivery of the produce to the market demand.

As ethylene is a strong stimulator of ripening, previous attempts to improve shelf-life of tomato fruits involve selecting genetic variants with fruits which either produce less ethylene or are less sensitive to ethylene. This has resulted in the identification of a number of pleiotropic ripening mutants with improved shelf-life which have been characterised to different levels of detail (Giovannoni, J (2007) Current Opinion in Plant Biology 10, 283-289). For example the Never-ripe (NR) mutant has been shown to be mutated in an ethylene receptor gene which resulted in insensitvity to ethylene. Due to this mutation the fruits remain firm during postharvest storage but ripening and the associated development of colour and taste is blocked.

In addition, ripening-inhibitor (rin), non-ripening (nor) and colourless non-ripening (cnr) mutants have been identified which are modified in genes encoding transcription factors involved in the production of, or response to, ethylene.

Although mutants like rin have a certain practical value for a better shelf-life, there is still room for improvement. In a preferred situation increased shelf-life should be achieved without compromising positive ripening-associated quality traits like pigmentation, flavour, and texture.

For tomato fruit growth and development a number of consecutive phases can be discerned. The earliest phase is floral development. After pollination as a second phase, early fruit development takes place which is characterised by a high frequency of cell division. During the third phase, the fruit is rapidly increasing in size mainly due to cell expansion. At the end of the third phase the fruit reaches the mature green stage. During the fourth phase fruit ripening takes place which is characterised by a change in colour and flavour as well as fruit firmness and texture.

The build up of the characteristic red colour of the tomato fruit is caused by the accumulation of lycopene and carotene. In general, different colouration phases are distinguished: mature green, breaker, pink and red. The typical red pigmentation initiates at the breaker stage. Red ripe stage or red ripe harvested fruit stage is the stage where the fruit has reached its mature colour on the major part of the fruit. In addition, enzymatic activity leads to degradation of the middle lamellar region of the cell walls which leads to cell loosening which is manifested as softening and loss of texture of the fruit. Softening of the fruit is often measured as external resistance to compression which can be quantified for example by a penetrometer.

Detailed molecular and biochemical studies have shown activities like endo-polygalacturonase and pectin-methylesterase to be involved in fruit softening. Antisense inhibition of the genes encoding these enzymes generally did not result in an improvement of fruit firmness which demonstrates that other activities are involved in the overall softening process. In this respect, expansins related to fruit ripening have been identified as being involved in the fruit softening process. Antisense inhibition of a ripening associated expansin indeed resulted in a small reduction in the rate of fruit softening.

As an alternative approach to increase shelf-life of tomato fruits, deoxyhypusine synthase (DHS) was suppressed transgenically (Wang, T. et al (2005) Plant Physiology 138, 1372-1382). Fruits of transgenic plants showed normal ripening in terms of colouration but a reduction in postharvest softening and senescence related to the level of DHS suppression. Some of the events were free of wrinkling of the fruit skin for up to 44 days after harvest of the fruit at the breaker stage. However, strongly suppressed DHS events showed pleiotropic effects such as male sterility probably due to the fact that DHS modulates several translation initiation factors 5A (eIF-5A).

In addition, a naturally occurring mutation has been described called Delayed Fruit Deterioration (DFD) which is characterised by a very long shelf-life of up to 7 months (Saladie, M. et al (2007) Plant Physiology 144, 1012-1028). This mutant has a high resistance to external compression of the fruit and minimal water loss but internal tissues undergo a normal softening. This demonstrates that softening of fruit tissue and fruit firmness are not necessarily linked.

The conclusion of these studies is that probably different physiological processes are involved in the overall fruit softening process. Modification of single genes known to be involved in ripening has not yet resulted in a fruit with normal ripening but minimal tissue softening. The conclusion could be that it is physiologically not feasible to modify ripening this way.

Alternatively, as many genetic factors are involved in the ripening process it may be required to modify these genes simultaneously or the critical factor has not yet been identified.

As tomato is a climacteric fruit, the ripening phase is characterised by an enhanced ethylene production and respiratory burst. Respiration is the metabolic oxidation of sugars which leads to the release of $CO_2$. As a by-product of this respiratory activity reactive oxygen species (ROS) are formed which are very reactive and can cause significant damage to cell structures leading to oxidative stress. ROS are suggested to play an important role in the enhancement of senescence in both leaves and fruits. During the climacteric phase flavour (volatiles, sugars, acids) and colour compounds are formed which provide a tomato fruit its typical taste perception and appearance.

The senescence phase is the final ripening phase which is characterised by a further softening of the fruit tissue, increased respiration and water loss which further facilitates seed dispersal. Infection by opportunistic pathogens like Botrytis may occur relatively easy at this stage.

As tomato is climacteric, fruit can be picked at the mature green or breaker/pink stage after which the colouration and softening processes continue to take place postharvest. If required, the harvested immature fruits can be exposed to exogenous ethylene in order to enhance the ripening process. Given the important stimulating role of ethylene in the ripening process, efforts to increase shelf-life have focused on the ethylene biosynthesis, perception or effector genes in order to slow down fruit ripening. Both through selection of natural variation as well as through genetic engineering ethylene components have been modified successfully which has resulted in extended shelf-life through slowing down the ripening process. The down side of such approach is that desirable quality traits related to fruit ripening develop more slowly as well.

Senescence is a naturally occurring, developmental process at the end of a life cycle of a plant or plant organ like a leaf or a fruit. Well-known stimulating factors of senescence are developmental age, wounding, detachment, darkness, nutrient deficiency and hormones. Although ethylene is the plant hormone known to stimulate senescence other hormones like jasmonate may also contribute to this process. During the final stage of leaf development metabolism is reprogrammed in order to remobilize resources into reproductive structures like seeds.

Yellowing of leaves being the most visible symptom of senescence is a consequence of chlorophyll breakdown during a relatively late stage of senescence which can be enhanced by ethylene once a leaf is receptive. Senescence is also considered the terminal stage of fruit ripening. The process is characterised by extensive tissue softening, water loss and deterioration which can serve seed dispersal. In addition to ethylene biosynthesis and response, postharvest metabolism of detached fruit is characterised by a strong enhancement of respiration which as a consequence leads to the production of reactive oxygen species (ROS).

Oxidative stress is known to contribute significantly to senescence but as compared to ethylene has not been studied extensively for fruit ripening. One study describes a correlation of fruit deterioration and the level of ROS scavenging enzymes which at least suggests a functional role for these enzymes in fruit senescence (Mondal, K. et al (2004) Biologia Plantarum 48, 49-53).

Citation or identification of any document in this application is not an admission that such document is available as prior art to the present invention.

SUMMARY OF THE INVENTION

It is therefore the object of the invention to provide traits which extend the shelf-life of fruits by preventing or inhibiting fruit senescence, but which allow ripening processes to be completed as much as possible.

The method used to develop the new tomato of the present invention relates to the inhibition of senescence by selecting for plants with a higher level of resistance to oxidative stress caused by the herbicide paraquat. Given the complex spatial and temporal regulation of senescence it may be expected that many regulatory and effector genes are involved in senescence.

Although genetic studies have discovered a number of genes involved in both leaf and fruit senescence most of the genetic factors involved in senescence are currently still unknown. Therefore it was reasoned that a more unbiased approach is needed to be more successful in this respect. Such an approach may comprise the exposure of populations containing genetic variants to oxidative stress.

The present invention relates to a tomato plant, and the fruit, progeny, propagation material and germplasm thereof, having an improved shelf-life as compared to a wild type tomato plant. The tomato plant of the present invention may be obtaining by introgressing the increased shelf life trait from the mutant LePQ58 (deposit accession number NCIMB 41531) into a tomato plant with a normal shelf-life.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSITS

The Deposits with NCIMB Ltd., Ferguson Building, Craibstone Estate, Bucksburn, Aberdeen, AB21 9YA Scotland, UK, under deposit accession number NCIMB 41531 were made pursuant to the terms of the Budapest Treaty on 17 Dec. 2007. Upon issuance of a patent, all restrictions upon the deposit will be removed, and the deposit is intended to meet the requirements of 37 CFR §§1.801-1.809. The deposit will be irrevocably and without restriction or condition released to the public upon the issuance of a patent. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawings.

DETAILED DESCRIPTION OF THE INVENTION

Figure 1:
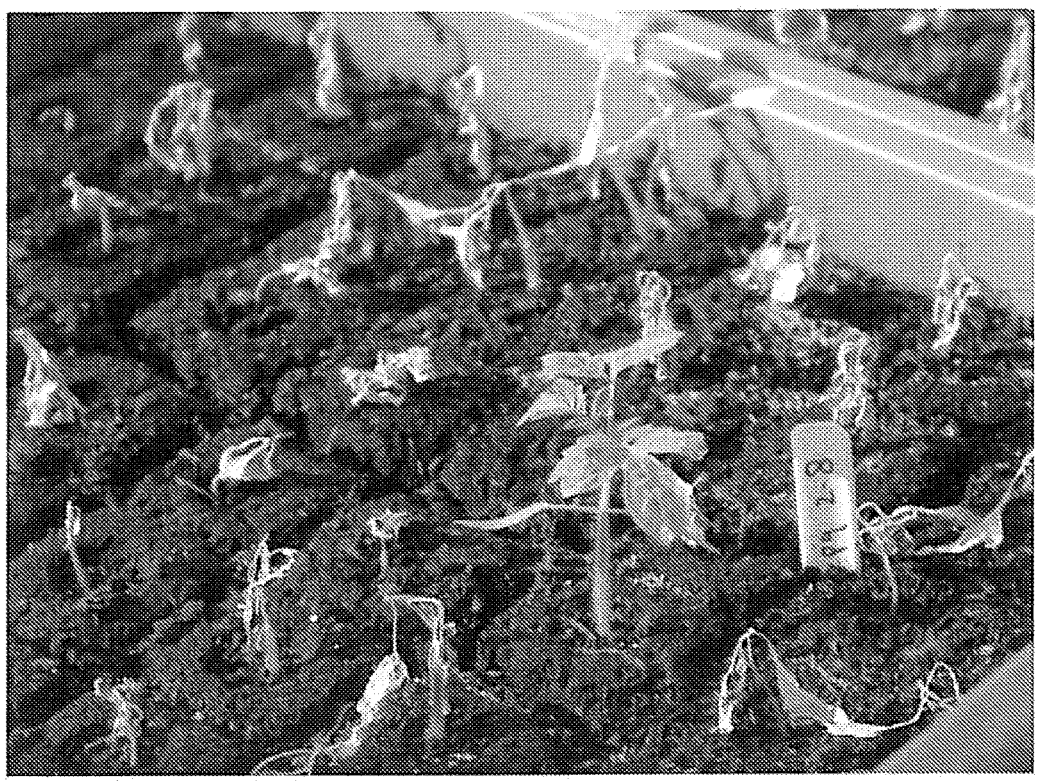
FIG. 1 shows an example of a M2 mutant of tomato which has survived a treatment using paraquat. The neighbouring plants have been completely killed by the herbicide.

Oxidative stress was applied by application of the herbicide paraquat (N,N'-Dimethyl-4,4'-bipyridinium dichloride). Paraquat has a low redox potential and is therefore readily reduced when applied to plants. This results in the formation of a radical ion of paraquat which generates superoxide radicals. The superoxide radicals cause significant oxidative damage and finally cell death. It was anticipated that plants which are resistant to paraquat and have a high level of oxidative stress resistance will also have an improved shelf life.

In the research that led to the invention a mutant population was thus screened by applying the herbicide paraquat. A new mutant was therein identified that showed paraquat resistance and a better shelf-life than found in wildtype tomato plants.

The invention thus relates to a tomato plant the fruits of which have an improved shelf-life as compared to the fruits of a wildtype tomato plant, obtainable by introgressing the improved shelf-life trait from the mutant LePQ58 (deposit accession number NCIMB 41531) into a tomato plant with a normal shelf-life.

The improved shelf-life trait of the invention is defined herein as a fruit firmness at red ripe harvest that is increased by at least 31%, preferably by at least 42%, more preferably by at least 52%, even more preferably by at least 60%, most preferably by at least 70% as compared to a fruit having similar genetic background that lacks the trait of the invention.

The improved shelf-life trait of the invention is furthermore defined as having a fruit firmness at 4 weeks post harvest that is decreased, when compared to the red ripe harvested fruit stage, by less than 50%, preferably by less than 43%, more preferably by less than 38%, even more preferably by less than 32%, most preferably by less than 25%. In addition the fruits of the invention show normal ripening, whereby colouration in pace and intensity is similar to the control. The fruit firmness is a resistance to external compression and is measured with a penetrometer, preferably model FT327, QA Supplies, Norfolk Va., as described in the examples.

A "wildtype" tomato plant is a tomato plant the fruit of which does not carry the trait of the invention. A control is a tomato plant having the same or a similar genetic background apart from the trait of the invention. Normal ripening, as used in this application, means that colouration in pace and intensity is similar to the control.

In this application the words "improved", "increased" and "extended" as used in conjunction with the word "shelf-life" are interchangeable and all mean having a better shelf-life, as expressed in a fruit firmness at red ripe harvest that is at least 31% firmer than a fruit having similar genetic background, and/or a firmness at 4 weeks post harvest that is decreased by less than 50%, and a ripening similar to the control.

"Introgressing" the trait as used in this application means that the trait is transferred from a parent to a progeny plant. Depending on the inheritance of the trait the progeny plant can be a first or further generation plant. Prerequisite is, however, that the progeny plant actually has acquired the trait of the invention, and thus phenotypically expresses the improved shelf-life trait. This can be tested by keeping the tomato fruits produced by the progeny plants for at least 4 weeks post harvest and testing the fruit firmness and colouration as described above.

The invention further relates to plants or plant parts, which have in their genome genetic information which is responsible for the extension of shelf-life and is found in the genome of the tomato plant LePQ58, the seeds of which were deposited under NCIMB accession number 41531.

The invention further relates to seed of the tomato plant of the invention and to parts of the plant. In one embodiment, the invention relates to plant parts that are suitable for sexual reproduction. Such parts are for example selected from the group consisting of microspores, pollen, ovaries, ovules, embryo sacs and egg cells. In addition the invention relates to parts of the plant that are suitable for vegetative reproduction, in particular cuttings, roots, stems, cells, protoplasts.

According to a further aspect thereof the invention provides a tissue culture of the tomato plant of the invention. The tissue culture comprises regenerable cells. Such tissue culture can be derived from leaves, pollen, embryos, cotyledon, hypocotyls, meristematic cells, roots, root tips, anthers, flowers, seeds and stems.

According to another aspect of the invention tomato plants are provided that have the same or similar increased shelf-life as tomato plants of the invention, of which representative seed was deposited under NCIMB Accession number NCIMB 41531, which plants are grown from seeds of the plant of the invention or regenerated from parts thereof, or from a tissue culture.

The invention also relates to progeny of the tomato plant of the invention. Such progeny can be produced by sexual or vegetative reproduction of a plant of the invention or a progeny plant thereof. The regenerated plant has the same or similar extended shelf-life as the claimed plant, of which representative seed was deposited under NCIMB Accession number NCIMB 41531. This means that such progeny has the same characteristics as claimed for the tomato plant of the invention, i.e. the increased shelf-life. In addition to this, the plant may be modified in one or more other characteristics. Such additional modifications are for example effected by mutagenesis or by transformation with a transgene.

Additionally the invention relates to the improvement of tomato plants which show an improved shelf-life due to known long-shelf-life genes, but which are decreased in ripening-related quality aspects such as slow ripening and reduced colour intensity as compared to wildtype tomato fruits, rendering them different from the trait of the invention.

The difference between the improved shelf-life trait of the invention and other shelf-life genes can, next to phenotypic observation of difference in ripening habit, easily be genetically established by carrying out an allelism assay. This comprises the crossing of the two events, which should be or should be made homozygous, and determining the phenotype of the resulting hybrid, and the subsequent F2 generation. In case of allelism of the events, the improved shelf life will be apparent in all plants of both the F1 and F2, i.e. the trait will not segregate. In case the phenotypes are determined by different loci, this will not be the case, and in the F1 and/or F2 segregation will be observed.

The invention thus relates to a tomato plant showing improved shelf life, obtainable by crossing a first tomato parent plant with a second tomato parent plant, wherein one of the parents is a plant grown from seeds of which a representative sample was deposited under NCIMB accession number 41531, or a progeny plant thereof, and selecting from the progeny of the cross tomato plants that show improved shelf life. The progeny from which selection is made is suitably F2 progeny.

The invention furthermore relates to hybrid seed and to a method for producing hybrid seed comprising crossing a first parent plant with a second parent plant and harvesting the resultant hybrid seed, wherein said first parent plant or said second parent plant is the plant of the invention. In case the trait is recessive, both parent plants need to be homozygous for the improved shelf-life trait in order for the hybrid seed to carry the trait of the invention. They need not necessarily be uniform for other traits.

In one embodiment, the invention relates to a tomato plant comprising the improved shelf-life trait, which plant is obtainable by:
 a) crossing a plant, representative seed of which was deposited with the NCIMB under accession number NCIMB 41531, with a plant not showing the trait to obtain an F1 population;
 b) selfing plants from the F1 population to obtain an F2 population;
 c) selecting in said F2 for plants producing fruits that have the same or a similar increased shelf-life as the tomato fruits of the invention; and
 d) optionally repeating steps b) and c).

It is clear that the parent that provides the trait of the invention is not necessarily a plant grown directly from the deposited seeds. The parent can also be a progeny plant from the seed or a progeny plant from seeds that are identified to have the genetic information of the trait of the invention by other means, such as molecular markers.

Progeny of the plants as claimed are also part of this invention. "Progeny" as used herein is intended to encompass all plants having the same or a similar extension of shelf-life as the original plants described herein and being derived therefrom in any way, such as by crossing, haploid culture, protoplast fusion or other techniques. Such progeny is not only the first but also all further generations as long as the extension of shelf-life is retained.

The invention further relates to germplasm and the use of germplasm containing genomic regions conferring the increased shelf-life of the invention for introgression into other germplasm in a breeding program.

Representative seeds of the new tomato plant (*Solanum lycopersicum*) were deposited on 17 Dec. 2007 with NCIMB Ltd., Ferguson Building, Craibstone Estate, Bucksburn, Aberdeen, AB21 9YA Scotland, UK and given the accession number NCIMB 41531.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Genetic Modification of Tomato Using Ems

Approximately 5000 seeds of the tomato line TO 029 (round tomato) were incubated in an aerated solution of either 0.05% (w/v) or 0.07% (w/v) ems during 24 hours at room temperature. After the ems treatment the M1 seeds were rinsed in water and planted in a greenhouse at 24° C. at 16 hours light, 8 hours dark regime to grow the mature plants and to induce flowering in order to produce M2 seeds.

After maturation, M2 seeds were harvested, bulked and stored until further use. The mutation frequency was estimated on the basis of the relative number of individual plants with a bleached phenotype which are disturbed in the chlorophyll biosynthesis.

Example 2

Screening for Paraquat Resistant Tomato Mutants

M2 seeds were sown in potting soil and plantlets were grown till the first true leaves had emerged. At this stage the plants were sprayed with a dose of paraquat which is lethal for sensitive tomato plants. Depending on de conditions but in general after 3 days the first necrotic symptoms on the leaves became visible. Approximately 7 days after the herbicide treatment, sensitive tomato plants are completely necrotic. At this stage the mutant plants that survived were labelled and considered putative paraquat resistant. A total number of 40.000 M2 plants were screened which resulted in 29 putative paraquat resistant mutants (FIG. 1).

The putative paraquat resistant tomato plants were grown to maturity in order to produce M3 seeds through self fertilisation.

Example 3

M3 Progeny Testing of Putative Paraquat Resistant M2 Mutants of Tomato

M3 seeds were harvested from the 29 putative paraquat resistant tomato plants. For each mutant 32 seeds were sown in potting soil and plantlets were raised in the greenhouse using standard tomato growing conditions. After emergence of the first true leaves the plants were sprayed with a dose of paraquat which is lethal to paraquat sensitive control tomato plants. Progeny which contained paraquat resistant plants were considered to be derived from true paraquat resistant M2 mutants.

Figure 2:
FIG. 2 shows an example of a M3 progeny screen of tomato M2 mutants which has survived a treatment using paraquat. Three blocks of plants are shown in this picture. On the right a fully sensitive mutant population (LePQ28) is shown which has been completely killed by paraquat. In the middle a fully resistant M3 population (LePQ19) is shown of which the plants have a normal habitus and which survived the treatment with paraquat. On the left a resistant M3 population (LePQ15) is shown of which the plants survived the treatment with paraquat but which have a dwarfed, bleached phenotype.

Some differences in response and phenotype were observed between the different M3 populations as illustrated in FIG. 2. Some progeny plants showed a fully resistant phenotype and some turned out to be sensitive. Another group of progeny showed a dwarfed bleached phenotype. The progeny which showed a fully sensitive phenotype is assumed to be derived from an M2 plant which survived the paraquat treatment which was not the result of a mutation. Of the 29 M3 populations tested, 6 showed the dwarfed and bleached phenotype but which all survived the paraquat treatment. Of the other 23 M3 populations 5 populations contained plants which were surviving the treatment. All other events were sensitive.

The 5 paraquat resistant tomato events which showed a normal plant habitus were considered to be derived from a mutation in the M2 mutants which allowed survival after herbicide treatment. These events were labelled: LePQ19, LePQ37, LePQ48, LePQ58 and LePQ96.

Example 4

Leaf Senescence Assay of Paraquat Resistant Mutants of Tomato

In order to assess whether the paraquat resistance mechanisms which have been selected from the mutant population have an effect on leaf senescence, a detached leaf assay was performed. M3 plants of the 5 different paraquat resistant mutants and a wild-type control plant (starting line for the mutant population) were grown in the greenhouse. When the plants started flowering, 8-10 leaves were detached from the plants and incubated in a closed container in the dark at room temperature. In order to prevent the leaves from drying out, the leaves were placed on water-saturated cotton wool.

Figure 3:
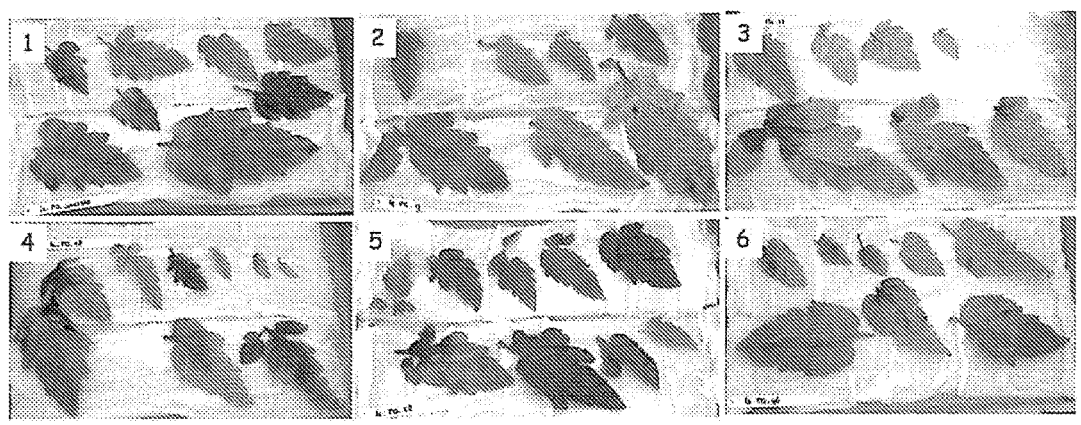
FIG. 3 shows a detached leaf assay to determine the rate of senescence of the paraquat resistance mutants of tomato. 1: wt control, 2: LePQ19, 3: LePQ37, 4: LePQ48, 5: LePQ58, 6: LePQ96.

After an incubation of two weeks senescence of the detached leaves became apparent. One of the paraquat events i.e.: LePQ58 showed a delay in the yellowing of the leaves indicating a reduced senescence response (FIG. 3).

Example 5

Figure 4:
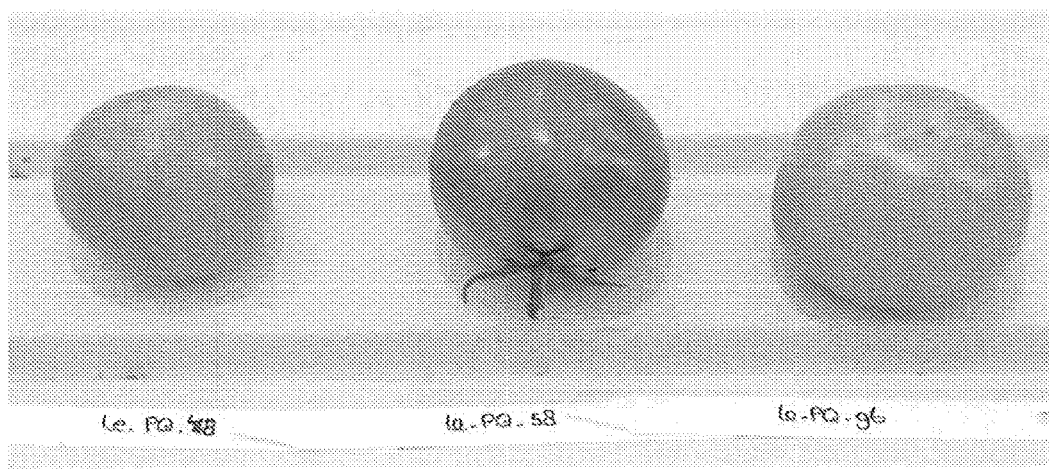
FIG. 4 shows the difference in green colour of mature green fruits of LePQ48 (left), LePQ58 (middle) and LePQ96 (right).

Mature Green Fruit Characteristic of Paraquat Resistant Mutants of Tomato which Show a Reduced Leaf Senescence The effect of the different paraquat resistance mutations in tomato were compared with respect to their degree of greening during the fruit expansion phase of fruit development. Mature green fruits of the LePQ58 mutant showed a clear difference to the wild type and other paraquat resistant mutants with respect to the intensity of the green colour which the fruits developed. LePQ58 fruits showed a more dark green colour at the mature green phase than the wild type controls and the other paraquat resistant mutants as shown in FIG. 4.

Example 6

Fruit Shelf-Life Assay of Paraquat Resistant Mutants of Tomato

In order to assess whether the paraquat resistance mechanisms which have been selected from the mutant population have an effect on fruit senescence, a shelf-life assay was performed. M3 plants of the 5 different paraquat resistant mutants and a wild-type control plant (starting line for the mutant population) were grown in the greenhouse.

Figure 5:
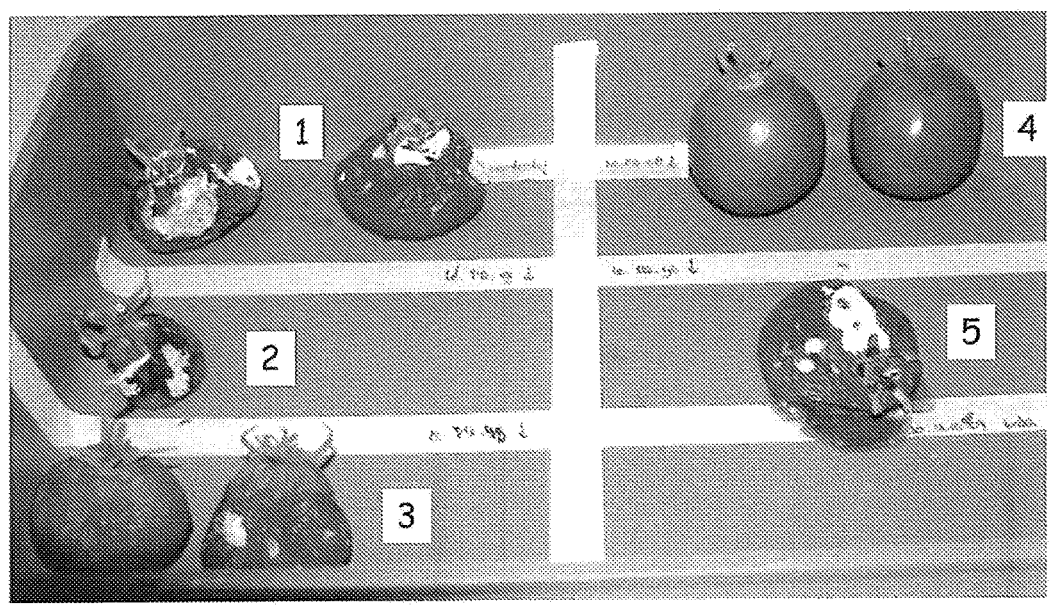
FIG. 5 shows the shelf-life assay of tomato fruits of control plants (1) and fruit of mutants LePQ19 (2), LePQ49 (3), LePQ58 (4) and LePQ96 (5). The fruits were harvested at the mature red stage. The picture is taken after 56 days of storage of the fruits at room temperature.

After fruit set and initial phases of fruit ripening had occurred fruits were picked from the plant at the red ripe stage and stored at room temperature. The fruits picked from the control plants and the mutants LePQ19, LePQ37, LePQ48, LePQ96 started to soften after approximately 14 days of storage whereas fruits from LePQ58 remained firm throughout this period. Prolonged storage resulted in further shrinking of the fruit, cracking of the skin and the occurrence of fortuitously occurring fungal infections. Fruits from the mutant LePQ58 showed no sign of softening after a period of 56 days (FIG. 5).

Therefore, it is concluded that the mutant LePQ58 has an enhanced shelf-life of the fruit when harvested at the red ripe stage as compared to the control, LePQ19, LePQ37, LePQ48 and LePQ96.

Example 7

Post Harvest Fruit Firmness of the Tomato Long Shelf Life Mutant LePQ58

Plants of mutant LePQ58 and a negative control were grown in the greenhouse in order to produce fruits to determine post harvest fruit firmness. As a negative control plants are used from the same population as the one from which mutant LePQ58 was isolated but which are sensitive to paraquat. Fruits were harvested at the red ripe stage and stored during the experiment at 21° C. in the greenhouse. Directly after harvest as well as 4 and 6 weeks post harvest the firmness of the fruits was determined using a penetrometer (model FT327, QA Supplies, Norfolk Va.). For each measurement a number of fruits were used to determine the pressure ($Kg/cm^2$) required to be imposed by the penetrometer in order to break the skin of the fruit. Such measurement is considered to reflect overall fruit firmness. The results are summarized in Table 1.

TABLE 2

Post harvest fruit firmness determination for LePQ58 as compared to the F1 hybrid Mecano. At 4 weeks post harvest the firmness of LePQ58, Mecano and control fruits expressed in Kg/cm2 was determined using a penetrometer. The average value for the indicated number of fruits is given.

| | 4 weeks post-harvest | | |
|---|---|---|---|
| | Fruit firmness ($Kg/cm^2$) | # of fruits | stdev |
| Control | 1.0 | 6 | 0.4 |
| LePQ58 | 2.9 | 7 | 0.6 |
| Mecano | 1.7 | 15 | 0.7 |

The results show that the fruits of LePQ58 have a higher fruit firmness 4 weeks post harvest as compared to the fruits of Mecano. The fruits of Mecano on the other hand have a high fruit firmness as compared to the negative control. From this experiment it is concluded that LeQP58 fruits have a higher post harvest firmness as compared to the current market standard.

Example 8

Post Harvest Fruit Weight Loss of the Tomato Long Shelf Life Mutant LePQ58

Weight loss as a result of evaporation is considered an important quality trait of stored tomato fruits. Fruits of the mutant LePQ58 as well as the negative control were harvested at the red ripe stage and stored during the experiment at 21 C. As a negative control plants are used from the same population as the one from which mutant LePQ58 was isolated but which are sensitive to paraquat. The fresh weight of 4 fruits of LePQ58 and the negative control was

TABLE 1

Post harvest fruit firmness determination for LePQ58. At 0, 4 and 6 weeks post harvest the firmness of LePQ58 and control fruits expressed in Kg/cm2 was determined using a penetrometer. The average value for the indicated number of fruits is given.

| | 0 weeks post-harvest | | | 4 weeks post-harvest | | | 6 weeks post-harvest | | |
|---|---|---|---|---|---|---|---|---|---|
| | Fruit firmness ($Kg/cm^2$) | # of fruits | stdev | Fruit firmness ($Kg/cm^2$) | # of fruits | stdev | Fruit firmness ($Kg/cm^2$) | # of fruits | stdev |
| Control | 3.1 | 3 | 0.4 | 1.0 | 6 | 0.4 | 0.1 | 3 | 0.0 |
| LePQ58 | 4.7 | 4 | 0.1 | 2.9 | 7 | 0.6 | 2.8 | 10 | 1.3 |

The results show that fruits harvested from LePQ58 were able to resist higher pressures imposed by the penetrometer at all post harvest time points, i.e. 0, 4 and 6 weeks, from which it can be inferred that fruits from LePQ58 have a higher firmness as compared to the negative control. It is further shown that the decline in fruit firmness during the post harvest storage period is smaller for LePQ58 fruits than for fruits of the negative control. As the colouration of the fruits of LePQ58 and the negative control are similar both in pace and intensity it is concluded that LePQ58 is a firm-ripening mutant.

In a second experiment the fruit firmness of LePQ58 was compared with the fruit firmness of an F1 hybrid variety called Mecano. Mecano produces firm ripening fruits and is considered the market standard with respect to shelf life. Harvested fruits of LePQ58, Mecano and the negative control were determined with respect to their post harvest firmness after 4 weeks of storage using the penetrometer as described above. The results are summarized in Table 2.

determined directly after harvest and after 4 weeks of storage. The result of the experiment is summarised in Table 3.

TABLE 3

Post harvest fruit weight loss determination for LePQ58 as compared to the negative control. At 0 and 4 weeks post harvest the fresh weigh of fruits of LePQ58 and negative control were determined

| | 0 weeks post-harvest | | 4 weeks post-harvest | | |
|---|---|---|---|---|---|
| | Fruit weight (g) | # of fruits | Fruit weight (g) | # of fruits | relative weight loss |
| Control | 224 | 4 | 111 | 4 | 50% |
| LePQ58 | 223 | 4 | 193 | 4 | 13% |

The results show that fruits of LePQ58 lost 13% of their fresh weight during 4 weeks of storage at room temperature whereas the negative control fruits lost 50% of their fresh weight. Therefore the LePQ58 mutant is considered to be strongly improved with respect to its resistance to post harvest weight loss due to evaporation.

The invention is further described by the following numbered paragraphs:

1. Tomato plant the fruits of which have an improved shelf-life as compared to the fruits of a wild type tomato plant, obtainable by introgressing the increased shelf life trait from the mutant LePQ58 (deposit accession number NCIMB 41531) into a tomato plant with a normal shelf-life.

2. Tomato plant of paragraph 1, wherein the increased shelf-life comprises a fruit that shows normal ripening having a fruit firmness at red ripe harvest that is increased by at least 31%, preferably by at least 42%, more preferably by at least 52%, even more preferably by at least 60%, most preferably by at least 70% as compared to a fruit having similar genetic background that lacks the trait of the invention.

3. Tomato plant of paragraph 1 or 2, wherein the increased shelf-life comprises a fruit that shows normal ripening and a firmness at 4 weeks post harvest that is decreased, when compared to red ripe harvested fruit stage, by less than 50%, preferably by less than 43%, more preferably by less than 38%, even more preferably by less than 32%, most preferably by less than 25%.

4. Tomato plant of any one of the paragraphs 1-3, which plant is a plant of which representative seed was deposited under deposit accession number NCIMB 41531.

5. A tomato plant comprising the improved shelf-life trait of any of the paragraphs 1-3, which plant is obtainable by:
    a) crossing a plant, representative seed of which was deposited with the NCIMB under accession number NCIMB 41531, with a plant not showing the trait to obtain an F1 population;
    b) selfing plants from the F1 population to obtain an F2 population;
    c) selecting in said F2 for plants producing fruits that have the same or a similar increased shelf-life as the tomato fruits of the invention; and
    d) optionally repeating steps b) and c).

6. Tomato fruit of a plant of any one of the paragraphs 1-5.

7. Progeny of a plant of any one of the paragraphs 1-5.

8. Propagation material of a plant of any one of the paragraphs 1-5.

9. Propagation material of paragraph 8, wherein the material is selected from microspores, pollen, ovaries, ovules, embryo sacs, egg cells, cuttings, roots, stems, cells, protoplasts, tissue cultures comprising regenerable cells, in particular derived from leaves, pollen, embryos, cotyledon, hypocotyls, meristematic cells, roots, root tips, anthers, flowers, seeds and stems.

10. Germplasm carrying an extended shelf-life trait, obtainable from the mutant LePQ58, representative seed of which was deposited under accession number NCIMB 41531.

11. Germplasm of paragraph 10, obtainable from a progeny plant of the mutant LePQ58, that still carries the extended shelf-life trait.

12. Use of the gerplasm of paragraph 10 or 11 in a breeding programme.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A tomato plant of mutant variety LePQ58, representative seed of which was deposited under accession number NCIMB 41531.

2. A method for producing a tomato plant the fruits of which have an improved shelf-life, comprising:
    a) crossing a parent plant of mutant variety LePQ58, representative seed of which was deposited with the NCIMB under accession number NCIMB 41531, with a second parent plant to obtain an F1 population;
    b) selfing the plant from the F1 population to obtain F2 population;
    c) selecting in said F2 for plants producing fruits that have an improvement in shelf-life as compared to the fruits of the second parent plant; and
    d) optionally repeating steps b) and c).

3. A tomato fruit of the mutant LePQ58 plant of claim 1, wherein said fruit has an improved shelf-life as compared to the fruit of a plant not comprising the genetic information in mutant LePQ58 responsible for the improved shelf-life.

4. A propagation material of the plant of claim 1.

5. The propagation material of claim 4, wherein the material comprises a microspore, pollen, ovary, ovule, embryo sac, egg cell, cutting, root, stem, cell, protoplast, tissue culture of regenerable cells, leaf, embryo, cotyledon, hypocotyl, meristematic cell, root tip, anther, flower, or seed.

6. A germplasm of the mutant variety LePQ58, representative seed of which was deposited under accession number NCIMB 41531.

7. A method for producing a tomato plant, comprising introgressing the germplasm of claim 6 into other germplasm in a breeding program, wherein the tomato plant produced in said breeding program comprises the genetic information from mutant LePQ58 responsible for producing fruit having an improved shelf-life as compared to the fruit of a plant not comprising the genetic information of mutant LePQ58.

* * * * *